(12) United States Patent
Lescop et al.

(10) Patent No.: US 11,390,615 B2
(45) Date of Patent: *Jul. 19, 2022

(54) CRYSTALLINE FORM OF THE COMPOUND (S)-3-{4-[5-(2-CYCLOPENTYL-6-METHOXY-PYRIDIN-4-YL)-[1,2,4]OXADIAZOL-3-YL]-2-ETHYL-6-METHYL-PHENOX

(71) Applicant: IDORSIA PHARMACEUTICALS LTD, Allschwill (CH)

(72) Inventors: Cyrille Lescop, Allswchill (CH); Jasper Dingemanse, Allswchill (CH); Andreas Krause, Allswchill (CH)

(73) Assignee: IDORSIA PHARMACEUTICALS LTD, Allschwil (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/070,876

(22) Filed: Oct. 14, 2020

(65) Prior Publication Data

US 2021/0024513 A1    Jan. 28, 2021

Related U.S. Application Data

(63) Continuation of application No. 16/503,245, filed on Jul. 3, 2019, now Pat. No. 10,836,754, which is a continuation of application No. 15/575,332, filed as application No. PCT/EP2016/061200 on May 19, 2016, now Pat. No. 10,385,043.

(30) Foreign Application Priority Data

May 20, 2015    (WO) ............. PCT/EP2015/061153

(51) Int. Cl.
| | | |
|---|---|---|
| C07D 413/04 | (2006.01) | |
| A61P 37/00 | (2006.01) | |
| A61K 31/047 | (2006.01) | |
| A61K 31/4245 | (2006.01) | |
| A61K 31/44 | (2006.01) | |
| G01N 23/20 | (2018.01) | |

(52) U.S. Cl.
CPC .......... *C07D 413/04* (2013.01); *A61K 31/047* (2013.01); *A61K 31/4245* (2013.01); *A61K 31/44* (2013.01); *A61P 37/00* (2018.01); *G01N 23/20075* (2013.01)

(58) Field of Classification Search
CPC ...... C07D 413/04; A61P 37/00; A61K 31/047
See application file for complete search history.

(56) References Cited

U.S. PATENT DOCUMENTS

| | | | |
|---|---|---|---|
| 3,647,809 A | 3/1972 | Reiter et al. | |
| 5,708,180 A | 1/1998 | Beck et al. | |
| 7,605,171 B2 | 10/2009 | Colandrea et al. | |
| 7,605,269 B2 | 10/2009 | Bolli et al. | |
| 7,687,491 B2 | 3/2010 | Nishi et al. | |
| 7,723,378 B2 | 5/2010 | Bolli et al. | |
| 7,750,040 B2 | 7/2010 | Bolli et al. | |
| 7,834,039 B2 | 11/2010 | Hobson et al. | |
| 7,846,964 B2 | 12/2010 | Bolli et al. | |
| 7,951,794 B2 | 5/2011 | Bolli et al. | |
| 7,981,924 B2 | 7/2011 | Bolli et al. | |
| 8,003,800 B2 | 8/2011 | Bolli et al. | |
| 8,039,644 B2 | 10/2011 | Bolli et al. | |
| 8,044,076 B2 | 10/2011 | Bolli et al. | |
| 8,133,910 B2 | 3/2012 | Bolli et al. | |
| 8,148,410 B2 | 4/2012 | Bolli et al. | |
| 8,178,562 B2 | 5/2012 | Bolli et al. | |
| 8,288,554 B2 | 10/2012 | Bolli et al. | |
| 8,299,086 B2 | 10/2012 | Bolli et al. | |
| 8,410,151 B2 | 4/2013 | Bolli et al. | |
| 8,575,200 B2 | 11/2013 | Bolli et al. | |
| 8,580,824 B2 | 11/2013 | Bolli et al. | |
| 8,592,460 B2 | 11/2013 | Bolli et al. | |
| 8,598,208 B2 | 12/2013 | Bolli et al. | |
| 8,658,675 B2 | 2/2014 | Bolli et al. | |
| 8,697,732 B2 | 4/2014 | Bolli et al. | |
| 9,133,179 B2 | 9/2015 | Bolli et al. | |
| 9,617,250 B2 | 4/2017 | Bolli et al. | |
| 10,385,043 B2 | 8/2019 | Lescop | |
| 2007/0021443 A1 | 1/2007 | Ohlmeyer et al. | |
| 2007/0043104 A1 | 2/2007 | Luthman et al. | |
| 2007/0270438 A1 | 11/2007 | Bhattacharya et al. | |
| 2008/0113961 A1 | 5/2008 | Nishi et al. | |
| 2008/0249093 A1 | 10/2008 | Colandrea et al. | |
| 2008/0300924 A1 | 12/2008 | Bolli et al. | |
| 2009/0275554 A1 | 11/2009 | Habashita et al. | |

FOREIGN PATENT DOCUMENTS

| | | |
|---|---|---|
| DE | 102 37 883 | 3/2004 |
| EP | 0 476 646 | 3/1992 |
| EP | 1 873 153 | 1/2008 |
| JP | 2008120794 | 5/2008 |
| WO | WO 91/15583 | 10/1991 |
| WO | WO 99/46277 | 9/1999 |
| WO | WO 00/45799 | 8/2000 |
| WO | WO 01/12627 | 2/2001 |
| WO | WO 02/068417 | 9/2002 |

(Continued)

OTHER PUBLICATIONS

Amin, S.S. et al., "Alopecia areata: A review," *Journal of the Saudi Society of Dermatology & Dermatologic Surgery*, vol. 17, pp. 37-45, (2013).

(Continued)

*Primary Examiner* — Kamal A Saeed

(74) *Attorney, Agent, or Firm* — Hoxie & Associates LLC

(57) ABSTRACT

The present invention relates to a crystalline form of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol.

19 Claims, 4 Drawing Sheets

(56) References Cited

FOREIGN PATENT DOCUMENTS

| | | |
|---|---|---|
| WO | WO 03/062248 | 7/2003 |
| WO | WO 03/062252 | 7/2003 |
| WO | WO 03/105771 | 12/2003 |
| WO | WO 2004/035538 | 4/2004 |
| WO | WO 2004/056789 | 7/2004 |
| WO | WO 2004/103279 | 12/2004 |
| WO | WO 2005/014525 | 2/2005 |
| WO | WO 2005/032465 | 4/2005 |
| WO | WO 2005/058848 | 6/2005 |
| WO | WO 2005/115382 | 12/2005 |
| WO | WO 2006/010544 | 2/2006 |
| WO | WO 2006/047195 | 5/2006 |
| WO | WO 2006/100631 | 9/2006 |
| WO | WO 2006/100633 | 9/2006 |
| WO | WO 2006/100635 | 9/2006 |
| WO | WO 2006/114400 | 11/2006 |
| WO | WO 2006/131336 | 12/2006 |
| WO | WO 2006/137019 | 12/2006 |
| WO | WO 2007/001973 | 1/2007 |
| WO | WO 2007/060626 | 5/2007 |
| WO | WO 2007/080542 | 7/2007 |
| WO | WO 2007/085451 | 8/2007 |
| WO | WO 2007/086001 | 8/2007 |
| WO | WO 2007/098474 | 8/2007 |
| WO | WO 2007/132307 | 11/2007 |
| WO | WO 2008/029306 | 3/2008 |
| WO | WO 2008/029370 | 3/2008 |
| WO | WO 2008/029371 | 3/2008 |
| WO | WO 2008/035239 | 3/2008 |
| WO | WO 2008/037476 | 4/2008 |
| WO | WO 2008/076356 | 6/2008 |
| WO | WO 2008/091967 | 7/2008 |
| WO | WO 2008/114157 | 9/2008 |
| WO | WO 2009/024905 | 2/2009 |
| WO | WO 2009/043889 | 4/2009 |
| WO | WO 2009/043890 | 4/2009 |
| WO | WO 2009/057079 | 5/2009 |
| WO | WO 2009/060278 | 5/2009 |
| WO | WO 2009/074950 | 6/2009 |
| WO | WO 2009/109872 | 9/2009 |
| WO | WO 2009/109904 | 9/2009 |
| WO | WO 2009/109906 | 9/2009 |
| WO | WO 2009/109907 | 9/2009 |
| WO | WO 2009/151529 | 12/2009 |
| WO | WO 2010/148649 | 12/2010 |
| WO | WO 2011/007324 | 1/2011 |
| WO | WO 2012/098505 | 7/2012 |
| WO | WO 2013/175397 | 11/2013 |
| WO | WO 2014/141171 | 9/2014 |
| WO | WO 2016/184939 | 11/2016 |

OTHER PUBLICATIONS

Ando, S. et al., "FTY720 exerts a survival advantage through the prevention of end-stage glomerular inflammation in lupus-prone BXSB mice," *Biochemical and Biophysical Research Communications*, vol. 394, pp. 804-810 (2010).
Behjati, M. et al., "Cardiovascular effects of fingolimod: A review article," *Iranian Journal of Neurology*, vol. 13, No. 3, pp. 119-126, (2014).
Bennett, J. et al., *Cecil Textbook of Medicine*, Part XIV, Oncology, Introduction, vol. 1, No. 20, pp. 1004-1010 (1996-1997).
Bigaud, M. et al., "Second generation S1P pathway modulators: Research strategies and clinical developments," *Biochimica et Biophysica Acta*, vol. 1841, pp. 745-758 (2014).
Bode, C. et al., "Immune Regulation by Sphingosine 1-Phosphate and Its Receptors," *Arch. Immunol. Ther. Exp.*, vol. 60, pp. 3-12, (2012).
Brack, A. et al., "Giant Cell Vasculitis Is a T Cell-Dependent Disease," *Molecullar Medicine*, vol. 3, No. 8, pp. 530-543, (1997).
Brinkmann, V., "FTY720: Mechanism of Action and Potential Benefit in Organ Transplantation," *Yonsei Medical Journal*, vol. 45, No. 6, pp. 991-997, (2004).
Buzard, D. et al., "Recent progress in the development of selective S1P1 receptor agonists for the treatment of inflammatory and autoimmune disorders," *Expert Opinion Ther. Patents*, vol. 18, No. 10, pp. 1141-1159, (2008).
Byrn, S. et al., "Pharmaceutical Solids: A Strategic Approach to Regulatory Considerations," Pharmaceutical Research, vol. 12, No. 7, pp. 945-954, (1995).
Caira, M. R, "Crystalline Polymorphism of Organic Compounds," Topics in Current Chemistry, vol. 198, pp. 163-208 (1998).
Chiba, K. "FTY720, a new class of immunomodulator, inhibits lymphocyte egress from secondary lymphoid tissues and thymus by agonistic activity at sphingosine 1-phosphate receptors," *Pharmacology & Therapeutics*, vol. 108, pp. 308-319, (2005).
Chiyo, M. et al., "Silencing S1P1 Receptors Regulates Collagen-V Reactive Lymphocyte-Mediated Immunobiology in the Transplanted Lung," *American Journal of Transplantation*, 2008, vol. 8, pp. 537-546, (2008).
Commodaro, A.G. et al., "Evaluation of Experimental Autoimmune Uveitis in Mice Treated with FTY720," *Investigative Ophthalmology & Visual Science*, vol. 51, No. 5, pp. 2568-2574, (2010).
D'Ambrosio, D. et al., "Ponesimod, a selective S1P1 receptor modulator: a potential treatment for multiple sclerosis and other immune-mediated diseases," *Therapeutic Advances in Chronic Disease*, vol. 7, No. 1, pp. 18-33, (2016).
Dermer, G., "Another Anniversary for the War on Cancer," *The Last Word*, Bio/Technology, vol. 12, pp. 320 (1 page), (1994).
English Machine Translation of Abstract of German Patent No. DE10237883, Title: "Substituierte Isoxazolderivate and ihre Verwendung in der Pharmazie," Obtained via Espacenet, Date Obtained: Sep. 19, 2019 (2 pages).
English Abstract of Japanese Publication No. JP 2008-120794, Title: "Pharmaceutical Composition Containing Heterocyclic Compound," Obtained via Espacenet, Date Obtained: Sep. 19, 2019 (2 pages).
Freshney, I., Chapter 1—Introduction, *Culture of Animal Cells*, pp. 1-6, (1983).
Gao, M. et al., "Prolonging Survival of Corneal Transplantation by Selective Sphingosine-1-Phosphate Receptor 1 Agonist," *PLoS ONE*, vol. 9, N. 9, pp. e105693, (2014).
Golub, T., et al., "The interaction between C5a and sphingosine-1-phosphate in neutrophils for antineutrophil cytoplasmic antibody mediated activation," *Arthritis Research & Therapy*, vol. 16: R142, pp. 1-12, (2014).
Hao, J. et al., "The interaction between C5a and sphingosine-1-phosphate in neutrophils for antineutrophil cytoplasmic antibody mediated activation," *Arthritis Research & Therapy*, vol. 16: R142, pp. 1-12, (2014).
Hirayama et al., "Yukikagobutsukessyo Sakuseihandobukku. Genri to Nouhau," Handbook for Preparing Organic Compound Crystal, pp. 17-23, 37-40, 45-51, and 57-65, (2008).
Hla, T. et al., "An Abundant Transcript Induced in Differentiating Human Endothelial Cells Encodes a Polypeptide with Structural Similarities to G-protein-coupled Receptors," *The Journal of Biological Chemistry*, vol. 265, No. 16, pp. 9308-9313, (1990).
Hla, T. et al., "Sphingosine 1-phosphate (S1P) Physiology and the effects of S1P receptor modulation," *Neurology*, vol. 76, No. 3, pp. S3-S8, (2011).
Hu, P.F. • p. F et al., "Sphingosine-1-phosphate: a potential therapeutic target for rheumatoid arthritis," *Mol Biol Rep*, vol. 38, pp. 4225-4230, (2011).
Huu, D.L. et al., "FTY720 Ameliorates Murine Sclerodermatous Chronic Graft-Versus-Host Disease by Promoting Expansion of Splenic Regulatory Cells and Inhibiting Immune Cell Infiltration into Skin," *Arthritis & Rheumatism*, vol. 65, No. 6, pp. 1624-1635, (2013).
International Search Report of International Application No. PCT/EP2016/061200, dated Jul. 11, 2016, 3 pages.
Japtok, L. et al., "Sphingosine-1-phosphate as signaling molecule in the skin," *Allergo J Int*, vol. 23, pp. 54-9, (2014).
Jo, S.K. et al., "Sphingosine-1-phosphate receptors: Biology and therapeutic potential in kidney disease," *Kidney International*, vol. 73, pp. 1220-1230, (2008).

(56) References Cited

OTHER PUBLICATIONS

Kappos, L. et al., "A Placebo-Controlled Trial of Oral Fingolimod in Relapsing Multiple Sclerosis," *The New England Journal of Medicine*, vol. 362, No. 5, pp. 387-401, (2010).

Kohno, T. et al., "A Novel Immunomodulator, FTY720, Prevents Spontaneous Dermatitis in NC/Nga Mice," *Biol. Pharm. Bull.*, vol. 27, No. 9, pp. 1392-1396 (2004).

Lessard, C.J. et al., "Variants at multiple loci implicated in both innate and adaptive immune responses are associated with Sjögren's syndrome," *Nat Genet.*, 2013, vol. 45, No. 11, pp. 1-26, (2013).

Li, C. et al., "Involvement of Sphingosine 1-Phosphate (SIP)/S1P$_3$ Signaling in Cholestasis-Induced Liver Fibrosis," *The American Journal of Pathology*, vol. 175, No. 4, pp. 1464-1472, (2009).

Lili, Y. at el., "Global Activation of CD8$^+$Cytotoxic T Lymphocytes Correlates with an Impairment in Regulatory T Cells in Patients with Generalized Vitiligo," *PLoS ONE*, 2012, vol. 7(5): eha513, pp. 1-10.

Lockwood, C.M. et al., "Remission induction in Behçt's disease following lymphocyte depletion by the anti-CD52 antibody CAMPATH 1-H," *Rheumatology*, vol. 42, pp. 1539-1544, (2003).

Meyer Zu Heringdorf, D. et al., "Pharmacology of the Sphingosine-1-Phosphate Signalling System," *Sphingolipids: Basic Science and Drug Development, Handbook of Experimental Pharmacology* 215, pp. 239-253, (2013).

Ongenae, K., "Evidence for an Autoimmune Pathogenesis of Vitiligo," *Pigment Cell Res*, vol. 16, pp. 90-100, (2003).

Patani, G.A. et al., "Bioisosterism: A Rational Approach in Drug Design," *Chem. Rev.*, vol. 96, No. 8, pp. 3147-3176, (1996).

Piali, L. et al., "The Selective Sphingosine 1-Phosphate Receptor 1 Agonist Ponesimod Protects against Lymphocyte-Mediated Tissue Inflammation," *The Journal of Pharmacology and Experimental Therapeutics*, vol. 337, No. 2, pp. 547-556, (2011).

Remington, The Science and Practice of Pharmacy, 21$^{st}$ Edition, 2005, Part 5, Pharmaceutical Manufacturing, 5 pages.

Roberts, E. et al., "Sphingosine 1-phosphate receptor agonists: a patent review (2010-2012)," *Expert Opinion Ther. Patents*, 2013, pp. 1-25.

Robinson, M., "Medical Therapy of Inflammatory Bowel Disease for the 21$^{st}$ Century," *Eur J Surg* 164, Suppl. 582, pp. 90-98, (1998).

Sanada, Y. et al., "Therapeutic Effects of Novel Sphingosine-1-Phosphate Receptor Agonist W-061 in Murine DSS Colitis," *PLoS ONE*, vol. 6(9): e23933, pp. 1-8, (2011).

Schürer, S.C. et al., "Ligand-Binding Pocket Shape Differences between Sphingosine 1-Phosphate (S1P) Receptors S1P$_1$ and S1P$_3$ Determine Efficiency of Chemical Probe Identification by Ultrahigh-Throughput Screening," *ACS Chemical Biology*, 2008, 13 pages.

Shamji, M.F. et al., "The pathogenesis of ankylosing spondylitis," *Neurosurg Focus*, vol. 24(1): E3, pp. 1-10, (2008).

Silverman, R.B., The Organic Chemistry of Drug Design and Drug Action, pp. 29-32, (2004).

Song, I.H. et al., "New treatment targets in ankylosing spondylitis and other spondyloarthritides," *Current Opinion in Rheumatology*, vol. 23, pp. 346-351, (2011).

Spiegel, S. et al., "The outs and the ins of sphingosine-1-phosphate in immunity," *Nature Reviews*, vol. 11, pp. 403-415, (2011).

Sui, M., "The sphingosine-1-phosphate receptor agonist FTY720 prevents the development of anti-glomerular basement membrane glomerulonephritis," *Mol Biol Rep*, vol. 39, pp. 389-397, (2012).

Van Der Giet, M. "Relevance and potential of sphingosine-1-phosphate in vascular inflammatory disease," *Biol. Chem.*, vol. 389, pp. 1381-1390, (2008).

Varadkar, S. et al., "Rasmussen's encephalitis: clinical features, pathobiology, and treatment advances," *Lancet Neurol.*, vol. 13, No. 2, pp. 195-205, (2014).

Wenderfer, S.E. et al., "Prolonged Survival and Reduced Renal Injury in MRL/lpr Mice Treated with a Novel Sphingosine-1-P Receptor Agonist," *Kidney Int.*, vol. 74, No. 10, pp. 1319-1326, (2008).

Yan, L. et al., "Discovery of 3-arylpropionic acids as potent agonists of sphingosine-1-phosphate receptor-1 (S1P$_1$) with high selectivity against all other known S1P receptor subtypes," *Bioorganic & Medicinal Chemistry Letters*, vol. 16, pp. 3679-3683 (2006).

Yin, X.D. et al., "Protective Effect of FTY720 on Several Markers of Liver Injury Induced by Concanavalin a in Mice," *Curr Ther Res Clin Exp.*, vol. 73, No. 4-5, pp. 140-149, (2012).

You, S. et al., "Therapeutic Use of a Selective S1P$_1$ Receptor Modulator Ponesimod in Autoimmune Diabetes," *PLoS ONE*, vol. 8(10): e77296, pp. 1-10, (2013).

Zhen, L. et al., "Discovery of Potent 3,5-Diphenyl-1,2,4-oxadiazole Sphingosine-1-phosphate-1 (S1P$_1$) Receptor Agonists with Exceptional Selectivity against S1P$_2$ and S1P$_3$," *Journal of Medicinal Chemistry*, vol. 48, No. 20, pp. 6169-6173, (2005).

Golub, T. et al., "Molecular Classification of Cancer: Class Discovery and Class Prediction by Gene Expression Monitoring," Science, 1999, 286, 531-537.

CRYSTALLINE FORM OF THE COMPOUND (S)-3-{4-[5-(2-CYCLOPENTYL-6-METHOXY-PYRIDIN-4-YL)-[1,2,4]OXADIAZOL-3-YL]-2-ETHYL-6-METHYL-PHENOX

CROSS REFERENCE TO RELATED APPLICATIONS

This application is a continuation application of U.S. application Ser. No. 16/503,245, filed Jul. 3, 2019, which is a continuation application of U.S. application Ser. No. 15/575,332, filed Nov. 17, 2017, which is a United States Application under 35 U.S.C. 371 claiming benefit of PCT Application No. PCT/EP2016/061200, filed on May 19, 2016, which claims the benefit of PCT Application No. PCT/EP2015/061153, filed on May 20, 2015, the contents of each of which are incorporated herein by reference.

The present invention relates to a crystalline form of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol (said compound being hereinafter also referred to as "COMPOUND").

The preparation of (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol and the medicinal use thereof is described in the published PCT applications WO 2011/007324 and WO 2013/175397. (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol can also be prepared as described below in Example 1.

The aim of the present invention was to provide crystalline forms of COMPOUND, and in particular crystalline forms with advantageous properties. Such advantageous properties may include higher melting points, better flow properties, higher thermodynamic stability, less hygroscopicity, different solubility, higher purity, better reproducibiliy in manufacturing (for example better filtration parameters and better reproducibility of formation of the solid), defined morphology, and/or better long-term stability. It has now been found that the crystalline form A of COMPOUND as described herein has advantageous properties.

Figure 1:
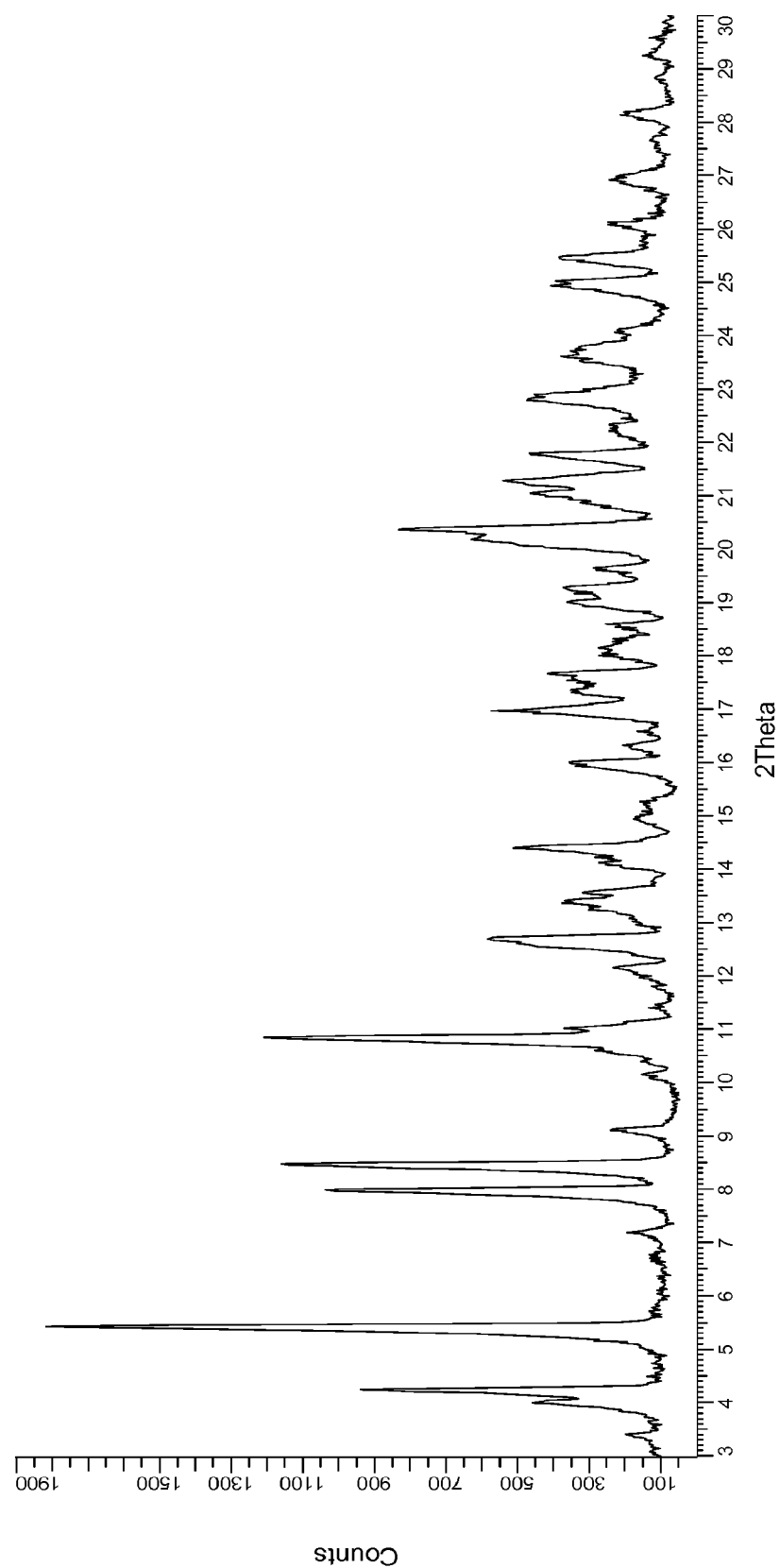
FIG. 1 shows the X-ray powder diffraction diagram of COMPOUND in the crystalline form A, wherein the X-ray powder diffraction diagram is displayed against Cu Kα1 radiation. In the diagram the angle of refraction 2θ is plotted on the horizontal axis and the counts on the vertical axis. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger than 10% are reported): 4.0° (18%), 4.2° (46%), 5.4° (100%), 8.0° (59%), 8.5° (68%), 9.1° (12%), 10.8° (72%), 12.7° (31%), 13.4° (18%), 13.6° (15%), 14.4° (28%), 16.0° (18%), 17.0° (31%), 17.3° (15%), 17.7° (22%), 19.0° (15%), 19.3° (17%), 20.4° (47%), 21.0° (22%), 21.3° (26%), 21.8° (22%), 22.8° (23%), 25.0° (20%), and 25.5° (19%).
Figure 2:
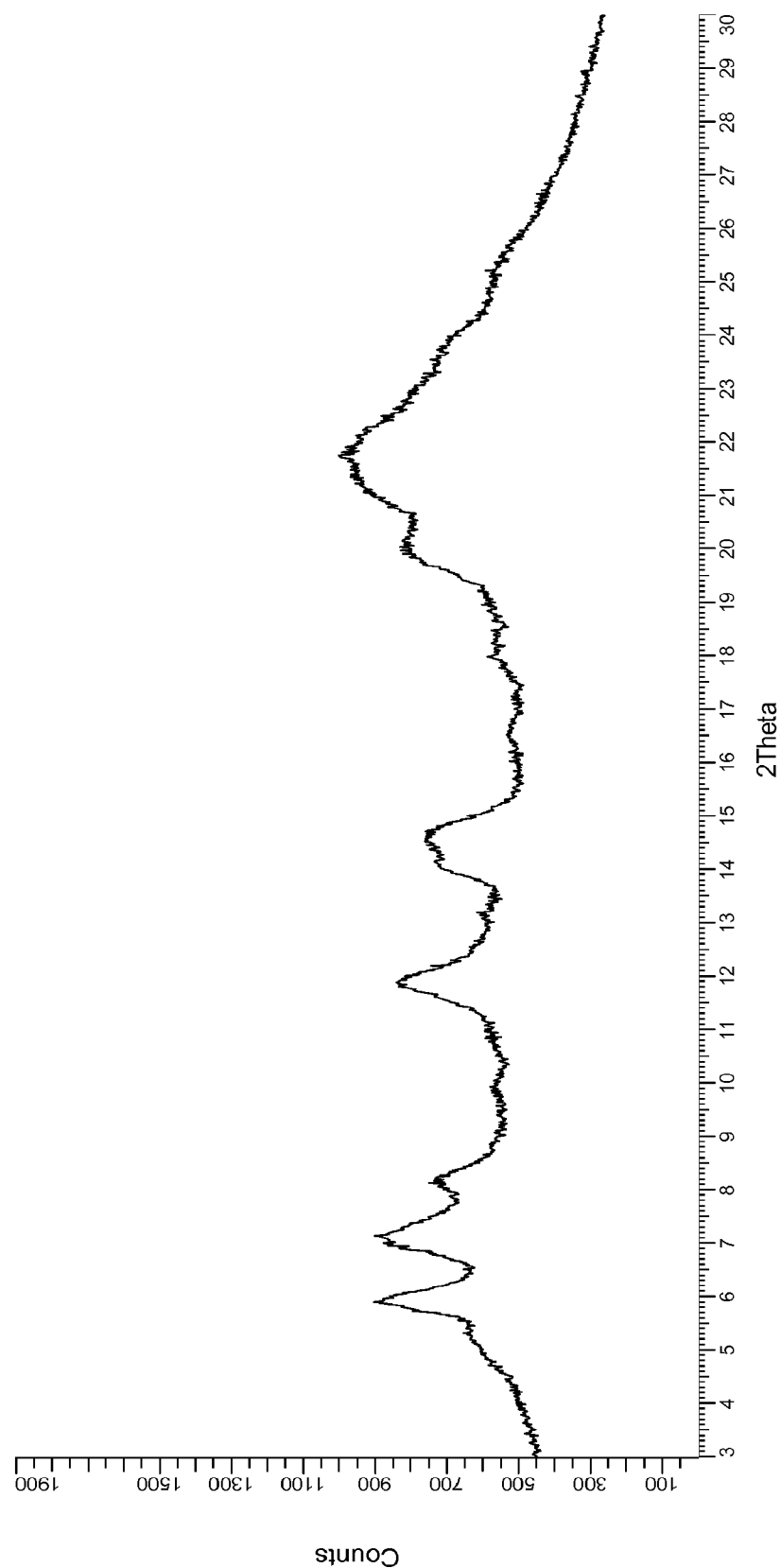
FIG. 2 shows the X-ray powder diffraction diagram of COMPOUND in the crystalline form B, wherein the X-ray powder diffraction diagram is displayed against Cu Kα1 radiation. In the diagram the angle of refraction 2θ is plotted on the horizontal axis and the counts on the vertical axis. The X-ray diffraction diagram shows very broad peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger than 10% are reported): 5.9° (74%), 7.1° (70%), 8.1° (35%), 11.9° (61%), 14.6° (48%), 20.1° (65%), and 21.5° (100%).
Figure 3:
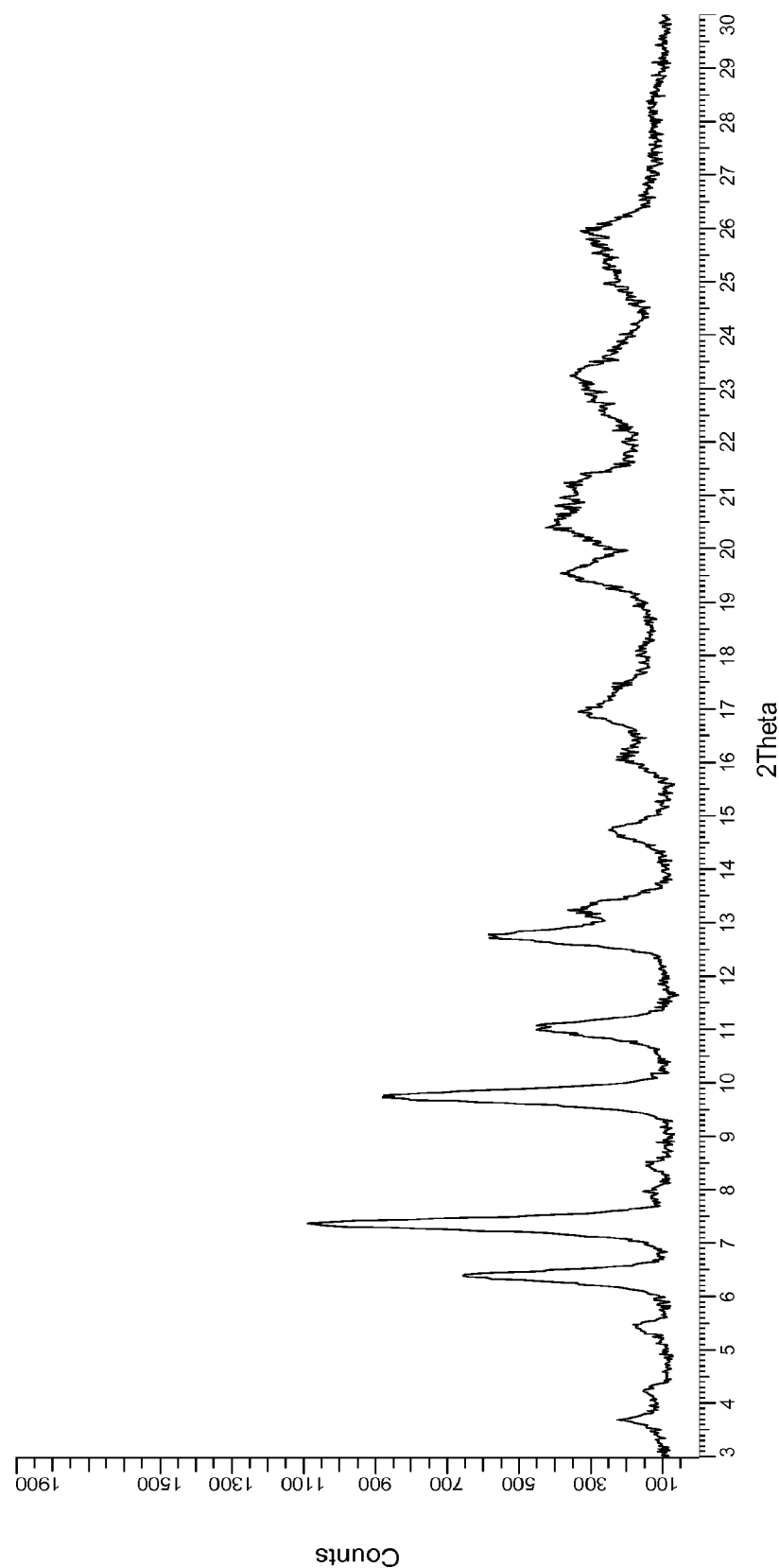
FIG. 3 shows the X-ray powder diffraction diagram of COMPOUND in the crystalline form C, wherein the X-ray powder diffraction diagram is displayed against Cu Kα1 radiation. In the diagram the angle of refraction 2θ is plotted on the horizontal axis and the counts on the vertical axis. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger than 10% are reported): 3.7° (11%), 6.4° (55%), 7.4° (100%), 9.8° (77%), 12.8° (49%), 13.2° (28%), 14.7° (15%), 17.0° (24%), 19.5° (24%), 20.5° (22%), 21.2° (19%), 23.3° (17%), and 25.9° (20%).

For the avoidance of any doubt, the above-listed peaks describe the experimental results of the X-ray powder diffraction shown in FIGS. 1 to 3. It is understood that, in contrast to the above peak list, only a selection of characteristic peaks is required to fully and unambiguously characterise the COMPOUND in the respective crystalline form of the present invention.

DESCRIPTION OF THE INVENTION

1) A first embodiment of the invention relates to a crystalline form, such as an essentially pure crystalline form, of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol, characterised by the presence of peaks in the X-ray powder diffraction diagram at the following angles of refraction 2θ: 5.4°, 8.5°, and 10.8°.

2) In another embodiment the present invention relates to the crystalline form according to embodiment 1), characterised by the presence of peaks in the X-ray powder diffraction diagram at the following angles of refraction 2θ: 4.2°, 5.4°, 8.0°, 8.5°, and 10.8°.

3) In another embodiment the present invention relates to the crystalline form according to embodiment 1), characterised by the presence of peaks in the X-ray powder diffraction diagram at the following angles of refraction 2θ: 4.2°, 5.4°, 8.0°, 8.5°, 10.8°, 12.7°, 14.4°, 17.7°, 20.4°, and 21.3°.

4) In another embodiment the present invention relates to the crystalline form according to any one of embodiments 1) to 3), which essentially shows the X-ray powder diffraction pattern as depicted in FIG. 1.

5) In another embodiment the present invention relates to the crystalline form according to any one of embodiments 1) to 4), which has a melting point of about 79° C. as determined by differential scanning calorimetry using the method as described herein.

6) In another embodiment the present invention relates to a crystalline form, such as an essentially pure crystalline form, of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol obtainable by:

i) dissolving 20 mg of (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol in amorphous form in 0.1 mL ethyl acetate;
ii) adding 0.9 mL n-heptane gradually over 1 h; and
iii) letting it standing closed overnight at 20-25° C.; or
iv) mixing 25-30 mg of (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol in amorphous form with 5 mL ethyl acetate/n-heptane 1/9 (volume by volume) and heating to 70° C.; and
v) allowing the solution to cool to 20-25° C. and storing it overnight at 4° C.

7) In another embodiment the present invention relates to the crystalline form according to embodiment 6), characterised by the presence of peaks in the X-ray powder diffraction diagram at the following angles of refraction 2θ: 5.4°, 8.5°, and 10.8°.

8) In another embodiment the present invention relates to the crystalline form according to embodiment 6), characterised by the presence of peaks in the X-ray powder diffraction diagram at the following angles of refraction 2θ: 4.2°, 5.4°, 8.0°, 8.5°, and 10.8°.

9) In another embodiment the present invention relates to the crystalline form according to embodiment 6), characterised by the presence of peaks in the X-ray powder diffraction diagram at the following angles of refraction 2θ: 4.2°, 5.4°, 8.0°, 8.5°, 10.8°, 12.7°, 14.4°, 17.7°, 20.4°, and 21.3°.

10) In another embodiment the present invention relates to the crystalline form according to embodiment 6), which essentially shows the X-ray powder diffraction pattern as depicted in FIG. 1.

11) In another embodiment the present invention relates to the crystalline form according to any one of embodiments 6) to 10), which has a melting point of about 79° C. as determined by differential scanning calorimetry using the method as described herein.

12) In another embodiment the present invention relates to the crystalline form according to any one of embodiments 1) to 5), obtainable by the processes of embodiment 6).

Based on the dependencies of the different embodiments 1) to 12) as disclosed hereinabove, the following embodiments are thus possible and intended and herewith specifically disclosed in individualised form:
1, 2+1, 3+1, 4+1, 4+2+1, 4+3+1, 5+1, 5+2+1, 5+3+1, 5+4+1, 5+4+2+1, 5+4+3+1, 6, 7+6, 8+6, 9+6, 10+6, 11+6, 11+7+6, 11+8+6, 11+9+6, and 11+10+6. Likewise embodiment 12) relates to the following embodiments herewith specifically disclosed in individualised form: 1 obtainable by 6, 2+1 obtainable by 6, 3+1 obtainable by 6, 4+1 obtainable by 6, 4+2+1 obtainable by 6, 4+3+1 obtainable by 6, 5+1 obtainable by 6, 5+2+1 obtainable by 6, 5+3+1 obtainable by 6, 5+4+1 obtainable by 6, 5+4+2+1 obtainable by 6, and 5+4+3+1 obtainable by 6.

In the list above the numbers refer to the embodiments according to their numbering provided hereinabove whereas "+" indicates the dependency from another embodiment. The different individualised embodiments are separated by commas. In other words, "5+4+1" for example refers to embodiment 5) depending on embodiment 4), depending on embodiment 1), i.e. embodiment "5+4+1" corresponds to embodiment 1) further characterised by the features of the embodiments 4) and 5). Moreover, "obtainable by 6" means that the indicated individualised embodiment is obtainable by the processes of embodiment 6).

Definitions provided herein are intended to apply uniformly to the subject matter as defined in any one of embodiments 1) to 12), and, mutatis mutandis, throughout the description and the claims unless an otherwise expressly set out definition provides a broader or narrower definition. It is well understood that a definition or preferred definition of a term or expression defines and may replace the respective term or expression independently of (and in combination with) any definition or preferred definition of any or all other terms or expressions as defined herein.

The term "essentially pure" is understood in the context of the present invention to mean especially that at least 90, preferably at least 95, and most preferably at least 99 percent by weight of (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol is present in the crystalline form A.

When defining the presence of a peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio of greater than x (x being a numerical value greater than 1), usually greater than 2, especially greater than 3.

In the context with stating that the crystalline form essentially shows an X-ray powder diffraction pattern as depicted in FIG. 1 the term "essentially" means that at least the major peaks of the diagram depicted in said figure, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the present application to an interval extending from X minus 10% of X to X plus 10% of X, and preferably to an interval extending from X minus 5% of X to X plus 5% of X. In the particular case of temperatures, the term "about" placed before a temperature "Y" refers in the present application to an interval extending from the temperature Y minus 5° C. to Y plus 5° C., and preferably to an interval extending from Y minus 3° C. to Y plus 3° C.

When specifying an angle of diffraction 2theta (2θ) for a peak in the present application, it should be understood that the value given is to be understood as an interval from said value minus 0.2° to said value plus 0.2°, and preferably from said value minus 0.1° to said value plus 0.1°.

The crystalline form A of the present invention can be used as medicament, e.g. in the form of pharmaceutical compositions for enteral or parenteral administration, such as especially oral administration, and is suitable for decreasing the number of circulating lymphocytes and for the prevention and/or treatment of a disease or disorder associated with an activated immune system in mammals, such as especially humans.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the crystalline form A of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

The crystalline form A of COMPOUND may be used as single component or as mixtures with other crystalline forms or the amorphous form of COMPOUND.

Diseases or disorders associated with an activated immune system which can be treated and/or prevented with the crystalline form A of the present invention are described for example in WO 2011/007324.

Preferred diseases or disorders to be treated and/or prevented with the crystalline form A of the present invention are selected from the group consisting of rejection of transplanted organs such as kidney, liver, heart, lung, pancreas, cornea, and skin; graft-versus-host disease; autoimmune syndromes including Sjögren's syndrome, spondylarthropathy/ankylosing spondylitis, juvenile arthritis, subacute cutaneous lupus, discoid lupus erythematosus, lupus nephritis, systemic sclerosis, diffuse cutaneous systemic sclerosis, vasculitis (e.g. M. Wegener), giant cell arteritis, Behcet disease, non-infectious uveitis, Goodpasture syndrome, Grave's disease, Guillain Barré syndrome, primary biliary cirrhosis, primary sclerosing cholangitis, autoimmune hepatitis, polymyositits, dermatomyositis, microscopic colitis, celiac disease, sarcoidosis, vitiligo, alopecia areata, chronic inflammatory demyelinating polyneuropathy (CIDP), Rasmussen's encephalitis, rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis, and systemic lupus erythematosus; atopic diseases such as rhinitis, conjunctivitis, and atopic dermatitis; asthma; type I diabetes; and post-infectious autoimmune diseases including rheumatic fever.

Very preferably the crystalline form A of the present invention is used to treat systemic lupus erythematosus.

The present invention also relates to a method for the prevention or treatment of a disease or disorder mentioned herein or mentioned in WO 2011/007324 comprising administering to a subject (especially a human subject) a pharmaceutically active amount of the crystalline form A of the present invention.

Furthermore, the crystalline form A of the present invention is also useful in combination with one or several immunomodulating agents, for the prevention and/or treatment of the diseases and disorders mentioned herein. According to a preferred embodiment of the invention, said agents are selected from the group consisting of immunosuppressants, corticosteroids, nonsteroidal anti-inflammatory drugs, cytotoxic drugs, adhesion molecule inhibitors, cytokines, cytokine inhibitors, cytokine receptor antagonists and recombinant cytokine receptors.

The present invention also relates to the use of the crystalline form A of the present invention for the preparation of a pharmaceutical composition, optionally for use in combination with one or several immunomodulating agents, for the prevention or treatment of the diseases and disorders mentioned herein or mentioned in WO 2011/007324.

(S)-3-{4-[5-(2-Cyclopentyl-6-methoxy-pyridin-4-yl)-[1,2,4]oxadiazol-3-yl]-2-ethyl-6-methyl-phenoxy}-propane-1,2-diol can be prepared for example as described in the published PCT application WO 2011/007324 (see in particular Example 2) or by using the preparation process as disclosed in the published PCT application WO 2013/175397. In particular the compound can also be prepared as described herein below.

Experimental Part

The following Examples illustrate the invention in more detail. Temperatures are given in degrees Celsius. If not stated otherwise, room temperature is in the range of 18-25° C., and percentages are given by weight.

Abbreviations as used herein:
a/a area per area
API active pharmaceutical ingredient
ca. approximately
DCM dichloromethane
DIPEA Hüning's base, diethylisopropylamine
DMF dimethylformamide
DMSO dimethylsulfoxide
DSC differential scanning calorimetry
eq. equivalent(s)
EtOAc ethyl acetate
EtOH ethanol
Fig. figure
h hour(s)
$^1$H-NMR hydrogen-1 nuclear magnetic resonance
HPLC high performance liquid chromatography
HPMC hydroxypropyl methylcellulose
LC-MS liquid chromatography-mass spectrometry
MeOH methanol
min minute(s)
m.p. melting point
RH relative humidity
rt room temperature
TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
$t_R$ retention time
XRPD X-ray powder diffraction Methods Used:
$^1$H-NMR
400 MHz, Bruker; chemical shifts are given in ppm relative to the solvent used.

X-Ray Powder Diffraction Analysis

X-ray powder diffraction patterns were collected on a Bruker D8 Advance X-ray diffractometer equipped with a Lynxeye detector operated with CuKa-radiation in reflection mode (coupled two Theta/Theta). Typically, the X-ray tube was run at of 40 kV/40 mA. A step size of 0.02° (2θ) and a step time of 76.8 sec over a scanning range of 3-50° in 2θ were applied. The divergence slit was set to fixed 0.3. Powders were slightly pressed into a silicon single crystal sample holder with depth of 0.5 mm and samples were rotated in their own plane during the measurement. Diffraction data are reported using Cu Kα1 (λ=1.5406 Å), after the Kα2 component has been stripped using the instrument evaluation software (EVA). The accuracy of the 2θ values as provided herein is in the range of +/−0.1-0.2° as it is generally the case for conventionally recorded X-ray powder diffraction patterns.

Differential Scanning Calorimetry (DSC)

DSC data were collected on a Mettler Toledo STARe System (DSC822e module, measuring cell with ceramic sensor and STAR software version 9.20) equipped with a 34 position auto-sampler. The instrument was calibrated for energy and temperature using certified indium. Typically 1-5 mg of each sample, in an automatically pierced aluminium pan, was heated at 10° C. min$^{-1}$, unless stated otherwise, from −20° C. to 280° C. A nitrogen purge at 20 mL min$^{-1}$ was maintained over the sample. Peak temperatures are reported for melting points.

Example 1

Preparation of (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol a) (R)—N-((2-Cyclopentyl-6-methoxyisonicotinoyl)oxy)-4-((2,2-dimethyl-1,3-dioxolan-4-yl)methoxy)-3-ethyl-5-methylbenzimidamide To a 30 L reactor is added 2-cyclopentyl-6-methoxy-isonicotinic acid (1.27 kg, 1 eq.; can be prepared e.g. as described in WO 2013/175397), DMF (17 mL) and DCM (18 L). To the suspension is added oxalyl chloride (534 mL, 1.1 eq.) at 20° C. over 30 min. The mixture is stirred for 30 min. The reaction is confirmed complete by LC-MS analysis. A solution of (R)-4-(2,2-dimethyl-[1,3]dioxolan-4-yl-methoxy)-3-ethyl-N-hydroxy-5-methyl-benzamidine (1.77 kg, 1 eq.; can be prepared as described in WO 2011/007324) and TEA (1.78 L, 2.2 eq.) in DCM (4 L) is added to the acid chloride at <30° C. over a period of 20 min. After stirring for 15 min the reaction is confirmed complete by LC-MS analysis. The reaction mixture is washed with water (7 L). Solvent (18 L) is removed at 55° C. and reduced pressure. EtOH (26 L) is added, the suspension cooled to 0° C. and filtered. The filter cake is washed with EtOH (7 L). The solid is dried on a rotary evaporator at 50° C. to yield an off-white solid. Yield: 2261 g (77%). LC-MS: purity: 100% a/a, $t_R$=1.886 min, $[M+1]^+$=512; $^1$H-NMR (CDCl$_3$): δ 7.43 (s, 2H), 7.34 (s, 1H), 7.12 (s, 1H), 5.16 (s, 2H), 4.52 (quint, J=5.8 Hz, 1H), 4.21 (dd, =8.3 Hz, J$_2$=6.9 Hz, 1H), 3.98 (s, 3H), 3.96 (m, 1H), 3.83 (m, 2H), 3.19 (m, 1H), 2.70 (m, 2H), 2.33 (s, 3H), 2.06 (m, 2H), 1.85 (m, 4H), 1.71 (m, 2H), 1.46 (d, J=21.3 Hz, 6H), 1.25 (t, J=7.6 Hz, 3H).

b) (R)-5-(2-Cyclopentyl-6-methoxypyridin-4-yl)-3-(4-((2,2-dimethyl-1,3-dioxolan-4-yl)methoxy)-3-ethyl-5-methylphenyl)-1,2,4-oxadiazole A mixture of (R)—N-((2-cyclopentyl-6-methoxyisonicotinoyl)oxy)-4-((2,2-dimethyl-1,3-dioxolan-4-yl)methoxy)-3-ethyl-5-methylbenzimidamide (2150 g, 1 eq.) in toluene (10 L) is heated to reflux for 4 h. Water is collected in a Dean Stark apparatus. The solution is concentrated to dryness at 70° C. and reduced pressure to yield a yellow oil. Yield: 2116 g (102%). LC-MS: purity: 96% a/a (4% a/a toluene), $t_R$=2.665 min, $[M+1]^+$=494; $^1$H-NMR (CDCl$_3$): δ 7.87 (d, J=6.3 Hz, 2H), 7.50 (s, 1H), 7.30 (s, 1H), 4.55 (quint, J=5.8 Hz, 1H), 4.23 (dd, =8.4 Hz, J$_2$=6.5 Hz, 1H), 4.01 (m, 4H), 3.90 (m, 2H), 3.24 (m, 1H), 2.77 (m, 2H), 2.40 (s, 3H), 2.09 (m, 2H), 1.88 (m, 4H), 1.73 (m, 2H), 1.50 (s, 3H), 1.48 (d, J=22.0 Hz, 6H), 1.32 (t, J=7.5 Hz, 3H).

LC-MS method used in steps a) and b):

Agilent G1956B (MS, Ionisation: ES1+, APCI), Agilent G1312B Bin Pump, Agilent G1315C DAD, Agilent G1316B (thermostated column compartment), Agilent G1367C (auto sampler). Injection volume: 2 μL; Column: Kinetex C18, 2.6 μm, 2.1×50 mm; Temperature: 40° C.; Flow: 1 mL/min; Gradient: Water/Acetonitrile: 95:5 to 5:95 in 2.8 min, then 95:5 in 0.2 min.

c) (S)-3-{4-[5-(2-Cyclopentyl-6-methoxy-pyridin-4-yl)-[1,2,4]oxadiazol-3-yl]-2-ethyl-6-methyl-phenoxy}-propane-1,2-diol To a 30 L Büchi reactor is added (R)-5-(2-cyclopentyl-6-methoxypyridin-4-yl)-3-(4-((2,2-dimethyl-1,3-dioxolan-4-yl)methoxy)-3-ethyl-5-methylphenyl)-1,2,4-oxadiazole (2.28 kg, 1 eq.) and EtOH (5 L). The solution is heated to 45° C. and 1 N HCl (3 L, 0.75 eq.) is added. The resulting mixture is stirred at 45° C. for 1 h and further for 3 h under reduced pressure (400 mbar). The mixture is neutralized with 32% NaOH (300 mL, 0.75 eq.) and concentrated at 60° C. and reduced pressure until the minimum stirring volume is reached (ca. 2 L). The reactor is set to normal pressure with nitrogen. The residue is diluted with EtOAc (20 L). The mixture is washed with water (2×10 L). The organic layer is concentrated at 60° C. and reduced pressure to yield a yellow oil.

Yield: 2053 g (98%). A second batch is produced; yield: 1907 g (98%).

Crystallization:

Both batches (2053 g+1907 g) are combined and dissolved in EtOAc (5.5 L) in a Pyrex flask (API solution). To a 30 L reactor is added (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol in crystalline form A (14 g) and n-heptane (30 L). The suspension is heated to 40° C. and the API solution is added over a period of 1 h at 40° C. The suspension is further stirred for 0.5 h, cooled to 20° C. and filtered over a 30 L Büchi nutsche. The product is washed with n-heptane (6 L). The product is dried on the nutsche applying a gentle nitrogen stream for two days.

Yield: 3300 g (83%), Purity (HPLC method): 99.51% a/a; m.p.: about 79° C. (DSC), COMPOUND in crystalline form A (FIG. 1).

$^1$H-NMR (D$_6$ DMSO): δ 7.78 (s, 2H), 7.53 (s, 1H), 7.26 (s, 1H), 4.98 (d, J=4.6 Hz, 1H), 4.65 (s, 1H), 3.94 (s, 3H), 3.86 (m, 2H), 3.75 (m, 1H), 3.50 (t, J=5.4 Hz, 2H), 3.28 (m, 1H), 2.75 (d, J=7.5 Hz, 2H), 2.35 (s, 3H), 2.03 (m, 2H), 1.81 (m, 4H), 1.69 (m, 2H), 1.22 (t, J=7.5 Hz, 3H).

HPLC Method:

HPLC system Agilent 1100; Injection volume: 5 μL; Column: Zorbax Eclipse XDB C18, 3.5 μm, 150 mm×4.6 mm; Temperature: 30° C.; Flow: 1 mL/min; Detection wavelength: 250 nm; Gradient: Water/Acetonitrile: 95:5 to 5:95 in 2.8 min, then 95:5 in 0.2 min. Eluent: Eluent A: water/MeOH/TFA (95/5/0.05), Eluent B: water/MeOH/TFA (5/95/0.05); Gradient: 0-1 min 40% A, 7-22 min 0% A, 22.1-27 min 40% A.

Figure 4:
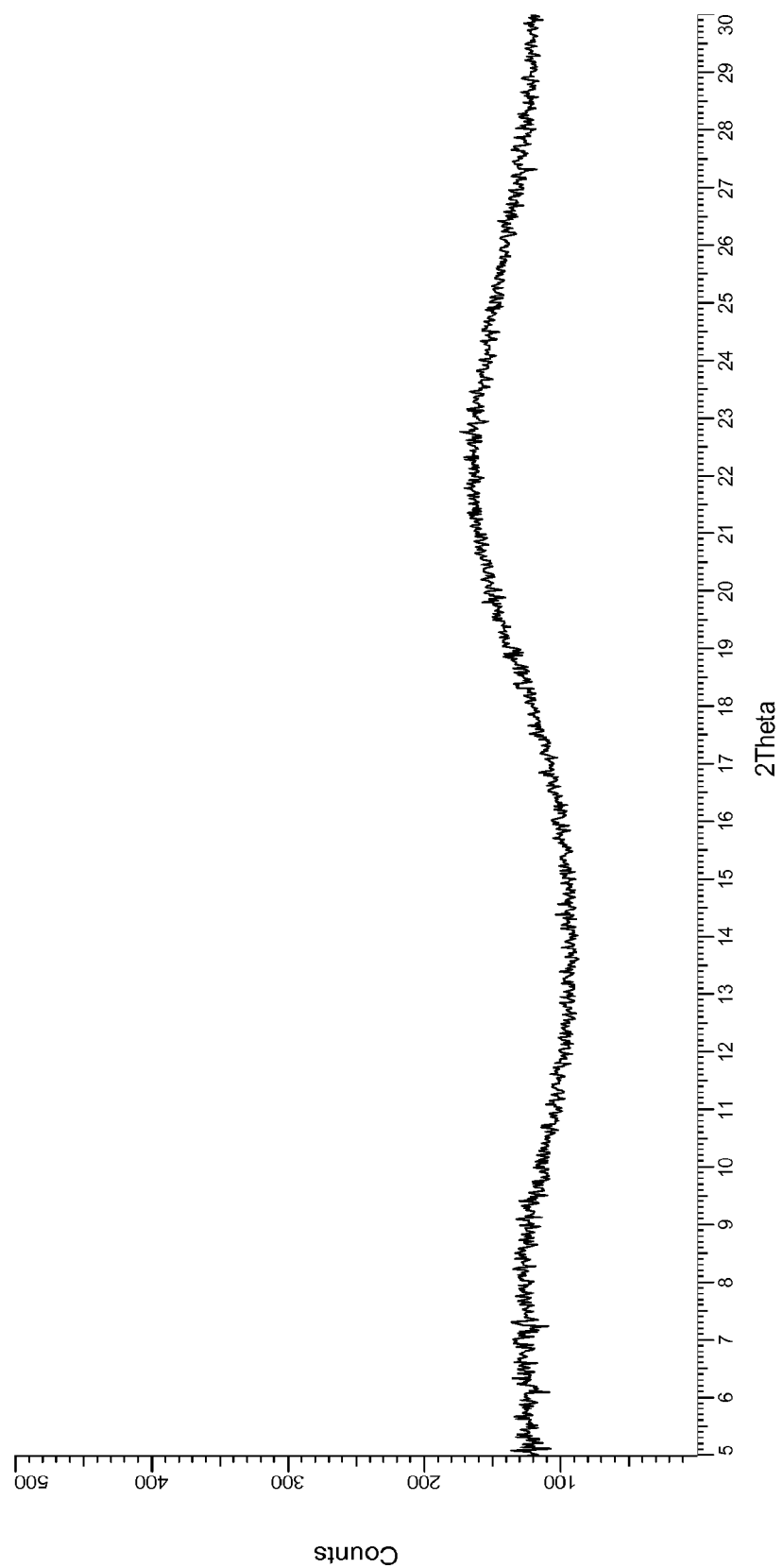
FIG. 4 shows the X-ray powder diffraction diagram of COMPOUND in the amorphous state, wherein the X-ray powder diffraction diagram is displayed against Cu Kα1 radiation. In the diagram the angle of refraction 2θ is plotted on the horizontal axis and the counts on the vertical axis. The X-ray diffraction shows a typical diagram as obtained for amorphous materials.

Preparation of Amorphous COMPOUND:

Amorphous COMPOUND is obtainable by the process described for Example 2 of the published PCT application WO 2011/007324. Said process is as follows:

a) To a solution of 2-cyclopentyl-6-methoxy-isonicotinic acid (162 mg, 0.732 mmol) in DMF (2 mL) and THF (10 mL), DIPEA (189 mg, 251 μL, 1.46 mmol) followed by TBTU (235 mg, 0.732 mmol) is added. The mixture is stirred at rt for 10 min before (R)-4-(2,2-dimethyl-[1,3]dioxolan-4-ylmethoxy)-3-ethyl-N-hydroxy-5-methyl-benzamidine (226 mg, 0.732 mmol) is added. The mixture is stirred at rt for 1 h before it is diluted with EtOAc and washed with water. The organic layer is separated and concentrated. The residue (375 mg) is dissolved in dioxane (10 mL) and the mixture is heated to 105° C. for 18 h. The mixture is cooled to rt, concentrated and the crude product is purified on preparative TLC plates (silica gel, 0.5 mm) using DCM containing 10% of methanol to give 4-{3-[4-((R)-2,2-dimethyl-[1,3]dioxolan-4-ylmethoxy)-3-ethyl-5-methyl-phenyl]-[1,2,4]oxadiazol-5-yl}-2-cyclopentyl-6-methoxy-pyridine (396 mg) as a yellow oil; LC-MS: $t_R$=1.39 min, $[M+H]^+$=494.31.

b) A solution of 4-{3-[4-((R)-2,2-dimethyl-[1,3]dioxolan-4-ylmethoxy)-3-ethyl-5-methyl-phenyl]-[1,2,4]oxadiazol-5- yl}-2-cyclopentyl-6-methoxy-pyridine (390 mg, 790 µmol) in 4 M HCl in dioxane (16 mL) is stirred at rt for 90 min before it is concentrated. The crude product is purified on preparative TLC plates using DCM containing 10% of methanol to give (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol (80 mg) as an off-white foam; LC-MS: $t_R$=1.20 min, [M+H]$^+$=454.32; $^1$H-NMR (400 MHz, CDCl$_3$): δ 7.91 (d, J=2.0 Hz, 1H), 7.89 (d, J=2.0 Hz, 1H), 7.53 (d, J=0.8 Hz, 1H), 7.32 (d, J=1.0 Hz, 1H), 4.16-4.22 (m, 1H), 4.03 (s, 3H), 3.96-3.99 (m, 2H), 3.93 (dd, $J_1$=4.3 Hz, $J_2$=11.3 Hz, 1H), 3.88 (dd, $J_1$=5.5 Hz, $J_2$=11.3 Hz, 1H), 3.21-3.31 (m, 1H), 2.79 (q, J=7.6 Hz, 2H), 2.74 (s br, 1H), 2.43 (s, 3H), 2.07-2.17 (m, 2H), 1.85-1.96 (m, 4H), 1.70-1.81 (m, 2H), 1.34 (t, J=7.5 Hz, 3H); XRPD diagram as shown in FIG. 4.

In the above description for the preparation of amorphous COMPOUND the compounds were characterised by $^1$H-NMR (Bruker Avance II, 400 MHz UltraShield™, 400 MHz ($^1$H), 100 MHz ($^{13}$C); chemical shifts are reported in parts per million (ppm) relative to tetramethylsilane (TMS), and multiplicities are given as s (singlet), d (doublet), t (triplet), q (quartet), quint (quintuplet), h (hextet), hept (heptuplet) or m (multiplet), br=broad, coupling constants are given in Hz); and/or by LC-MS Finnigan MSQ™ plus or MSQ™ surveyor (Dionex, Switzerland), with Agilent G4220A pump and AGilent G4212A DAD (Agilent, Switzerland), column: Zorbax RRHD SB-AQ, 1.8 µm, 3.0×20 mm (Agilent); gradient: 5-95% acetonitrile in water containing 0.04% of trifluoroacetic acid, within 1.2 min, flow: 1.6 mL/min; $t_R$ is given in min.

Compounds were purified by preparative TLC glass plates coated with silica gel 60 F$_{254}$ (0.5 mm).

Example 2: Preparation of Form A 20 mg of COMPOUND in amorphous form are dissolved in 0.1 mL EtOAc and 0.9 mL n-heptane are added gradually over 1 h. The formed solid is collected after standing closed overnight at 20-25° C. and consists of COMPOUND in the crystalline form A. Alternatively, 25-30 mg of COMPOUND in amorphous form is mixed with 5 mL EtOAc/n-heptane 1/9 (volume by volume) and heated to 70° C. The solution is allowed to cool to 20-25° C. and is then stored overnight at 4° C. The obtained solid is collected and is COMPOUND in the crystalline form A. By DSC a broad endothermic event is observed in the range of about 66° C. to about 88° C., with peak at about 79° C. (m.p. of crystalline form A).

Example 3: Preparation of Form B 0.5 g of COMPOUND in the crystalline form A, 2.5 mL DCM and 3 mL n-heptane are mixed and filtered into a petri dish (with diameter of approximately 9 cm). The solution is allowed to evaporate overnight at 20-25° C. The solid residue is collected and dried under vacuum (2 mbar for 1 h). The so obtained solid residue is COMPOUND in the crystalline form B as shown in FIG. 2. By DSC a broad endothermic event is observed in the range of about 44° C. to about 63° C., with peak at about 58° C. (m.p. of crystalline form B).

Example 4: Preparation of Form C

In a 15 mL brown glass vial 266 mg of COMPOUND in the crystalline form A and 36 mg of urea are dissolved in 10 mL methanol. The vial is left open at 20-25° C. for evaporation of the solvent. As soon as all solvent is evaporated and latest after 1 week 10 mL water is added and the sample is stirred by magnetic stirring at 20-25° C. for 5 days. The suspension is filtered and the recovered solid is dried at 2 mbar for 1 h. The so obtained solid residue is COMPOUND in the crystalline form C as shown in FIG. 3. By DSC a broad endothermic event is observed in the range of about 30° C. to about 60° C., with peak at about 48° C. (m.p. of crystalline form C).

Example 5: Comparison of Hygroscopicity of COMPOUND in Crystalline Forms A, B, and C Method:
Gravimetric Vapour Sorption (GVS) Analysis:
Measurements were performed simultaneously for the COMPOUND in the crystalline form A, B, and C on a multi sample instrument SPS-100n (Projekt Messtechnik, Ulm, Germany) operated in stepping mode at 25° C. The sample was allowed to equilibrate at 40% RH before starting a pre-defined humidity program (40-0-95-0-95-40% RH, steps of 5% ΔRH and with a maximal equilibration time of 24 hours per step were applied. About 20 to 30 mg of each sample was used. The hygroscopic classification is done according to the European Pharmacopeia Technical Guide (1999, page 86), i.e., non-hygroscopic: increase in mass is less than 0.2% mass/mass; slightly hygroscopic: increase in mass is less than 2% and equal to or greater than 0.2% mass/mass; hygroscopic: increase in mass is less than 15% and equal to or greater than 2% mass/mass. The mass change between 40% relative humidity and 80% relative humidity in the first adsorption scan is considered.
Form A: <0.2% mass gain: Non-hygroscopic
Form B: 0.5% mass gain: Slightly hygroscopic
Form C: 0.8% mass gain: Slightly hygroscopic

Example 6: Capsules Containing 0.5 mg, 1 mg, 2 mg, and 4 mg of COMPOUND in Crystalline Form A

| | Capsule for oral use | | | |
|---|---|---|---|---|
| Ingredients (mg) | 0.5 mg | 1 mg | 2 mg | 4 mg |
| Coated drug substance | | | | |
| COMPOUND in crystalline form A | 0.50 | 1.00 | 2.00 | 4.00 |
| Methylcellulose | 0.05 | 0.10 | 0.20 | 0.40 |
| Sodium lauryl sulfate | 0.001 | 0.002 | 0.004 | 0.008 |
| Dipalmitoyl phosphatidylcholine | 0.05 | 0.10 | 0.20 | 0.40 |
| Water, purified | 5.16 | 10.31 | 20.61 | 41.22 |
| Capsule blend | | | | |
| Methylcellulose | 0.16 | 0.30 | 0.62 | 1.25 |
| Sodium lauryl sulfate | 0.54 | 1.10 | 2.17 | 4.33 |
| Colloidal silicon dioxide | 2.49 | 2.60 | 2.78 | 2.67 |
| Mannitol | 352.2 | 368.8 | 388.8 | 368.5 |
| Capsules filling weight (mg) | 356 | 374 | 397 | 382 |

Due to very low aqueous solubility (about 0.06 µg/mL in water) and poor wetting ability of the active substance (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol, the drug substance is coated as a first step. To that extend, methylcellulose (METHOCEL™ A15 Premium LV, suspending agent), sodium lauryl sulfate and dipalmitoyl phosphatidylcholine (wetting agents) are added one after the other to purified water under stirring: each excipient is added only after complete dissolution of the former one. The API, i.e. COMPOUND in crystalline form A, is sieved through mesh size 40, added to the methocel solution and stirred for 3 h, until a complete homogenious suspension is formed. The suspension is spray dried (outlet air temperature 40-50° C., drying gas flow rate 110 kg/h, atomization $N_2$ gas flow rate 8 kg/h, $N_2$ atomization pressure 0.7 bar), which results in the coated API. The coating leads to an increase of the solubility of the active substance (about 29 µg/mL in water).

Once coated, the drug substance content is determined in the coated drug substance and the amount of material used in the next step eventually corrected accordingly.

The coated API is sieved together with methylcellulose (METHOCEL™ A15 Premium LV), sodium lauryl sulfate and a part of mannitol (EMPROVE® Parteck® M 200 Mannitol) and mixed. More mannitol portions are added after sieving to the blend in 2 steps, each time followed by mixing. The colloidal silicon dioxide (AEROSIL® 200) is then sieved together with the remainder of the mannitol and added to the powder blend. The final mixture is further blended. The powder is then filled in size "0", white-opaque HPMC capsules (VCaps+®).

The invention claimed is:

1. A method of treating multiple sclerosis comprising administering a pharmaceutically active amount of a crystalline form of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol to a subject in need thereof, wherein the crystalline form is characterized by the presence of peaks in the X-ray powder diffraction diagram at the following angles of refraction 2θ: 5.4°, 8.5°, and 10.8°.

2. The method according to claim 1, wherein the crystalline form of the compound is characterized by the presence of peaks in the X-ray powder diffraction diagram at the following angles of refraction 2θ: 4.2°, 5.4°, 8.0°, 8.5°, and 10.8°.

3. The method according to claim 1, wherein the crystalline form of the compound is characterized by the presence of peaks in the X-ray powder diffraction diagram at the following angles of refraction 2θ: 4.2°, 5.4°, 8.0°, 8.5°, 10.8°, 12.7°, 14.4°, 17.7°, 20.4°, and 21.3°.

4. The method according to claim 1, wherein the crystalline form of the compound has a melting point of about 79° C. as determined by differential scanning calorimetry.

5. The method according to claim 2, wherein the crystalline form of the compound has a melting point of about 79° C. as determined by differential scanning calorimetry.

6. The method according to claim 3, wherein the crystalline form of the compound has a melting point of about 79° C. as determined by differential scanning calorimetry.

7. A method of treating multiple sclerosis comprising administering a pharmaceutical composition to a subject in need thereof; wherein the pharmaceutical composition comprises a crystalline form of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol, wherein the crystalline form is characterized by the presence of peaks in the X-ray powder diffraction diagram at the following angles of refraction 2θ: 5.4°, 8.5°, and 10.8°; and wherein the pharmaceutical composition comprises about 2 mg or about 4 mg of the compound.

8. The method according to claim 7, wherein the pharmaceutical composition comprises about 2 mg of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol.

9. The method according to claim 7, wherein the pharmaceutical composition comprises about 4 mg of the compound (S)-3-{4-[5-(2-cyclopentyl-6-methoxy-pyridin-4-yl)-[1,2,4]oxadiazol-3-yl]-2-ethyl-6-methyl-phenoxy}-propane-1,2-diol.

10. The method according to claim 7, wherein the crystalline form of the compound is characterized by the presence of peaks in the X-ray powder diffraction diagram at the following angles of refraction 2θ: 4.2°, 5.4°, 8.0°, 8.5°, and 10.8°.

11. The method according to claim 8, wherein the crystalline form of the compound is characterized by the presence of peaks in the X-ray powder diffraction diagram at the following angles of refraction 2θ: 4.2°, 5.4°, 8.0°, 8.5°, and 10.8°.

12. The method according to claim 9, wherein the crystalline form of the compound is characterized by the presence of peaks in the X-ray powder diffraction diagram at the following angles of refraction 2θ: 4.2°, 5.4°, 8.0°, 8.5°, and 10.8°.

13. The method according to claim 7, wherein the crystalline form of the compound is characterized by the presence of peaks in the X-ray powder diffraction diagram at the following angles of refraction 2θ: 4.2°, 5.4°, 8.0°, 8.5°, 10.8°, 12.7°, 14.4°, 17.7°, 20.4°, and 21.3°.

14. The method according to claim 8, wherein the crystalline form of the compound is characterized by the presence of peaks in the X-ray powder diffraction diagram at the following angles of refraction 2θ: 4.2°, 5.4°, 8.0°, 8.5°, 10.8°, 12.7°, 14.4°, 17.7°, 20.4°, and 21.3°.

15. The method according to claim 9, wherein the crystalline form of the compound is characterized by the presence of peaks in the X-ray powder diffraction diagram at the following angles of refraction 2θ: 4.2°, 5.4°, 8.0°, 8.5°, 10.8°, 12.7°, 14.4°, 17.7°, 20.4°, and 21.3°.

16. The method according to claim 11, wherein the crystalline form of the compound has a melting point of about 79° C. as determined by differential scanning calorimetry.

17. The method according to claim 12, wherein the crystalline form of the compound has a melting point of about 79° C. as determined by differential scanning calorimetry.

18. The method according to claim 14, wherein the crystalline form of the compound has a melting point of about 79° C. as determined by differential scanning calorimetry.

19. The method according to claim 15, wherein the crystalline form of the compound has a melting point of about 79° C. as determined by differential scanning calorimetry.

* * * * *

UNITED STATES PATENT AND TRADEMARK OFFICE
CERTIFICATE OF CORRECTION

PATENT NO. : 11,390,615 B2
APPLICATION NO. : 17/070876
DATED : July 19, 2022
INVENTOR(S) : Cyrille Lescop et al.

It is certified that error appears in the above-identified patent and that said Letters Patent is hereby corrected as shown below:

On the Title Page

Item (54):
"(54) CRYSTALLINE FORM OF THE COMPOUND (S)-3-{4-[5-(2-CYCLOPENTYL-6-METHOXY-PYRIDIN-4-YL)-[1,2,4]OXADIAZOL-3-YL]-2-ETHYL-6-METHYL-PHENOX"
Should read:
-- (54) CRYSTALLINE FORM OF THE COMPOUND (S)-3-{4-[5-(2-CYCLOPENTYL-6-METHOXY-PYRIDIN-4-YL)-[1,2,4]OXADIAZOL-3-YL]-2-ETHYL-6-METHYL-PHENOXY}-PROPANE-1,2-DIOL --

In the Specification

Column 1, Lines 1-4:
"CRYSTALLINE FORM OF THE COMPOUND (S)-3-{4-[5-(2-CYCLOPENTYL-6-METHOXY-PYRIDIN-4-YL)-[1,2,4]OXADIAZOL-3-YL]-2-ETHYL-6-METHYL-PHENOX"
Should read:
-- CRYSTALLINE FORM OF THE COMPOUND (S)-3-{4-[5-(2-CYCLOPENTYL-6-METHOXY-PYRIDIN-4-YL)-[1,2,4]OXADIAZOL-3-YL]-2-ETHYL-6-METHYL-PHENOXY}-PROPANE-1,2-DIOL --

Column 1, Lines 48 and 65, and Column 2, Line 11:
"radiation. In the diagram the angle of refraction 20 is plotted"
Should read:
-- radiation. In the diagram the angle of refraction $2\theta$ is plotted --

Column 4, Line 46:
"When specifying an angle of diffraction 2theta (20) for a"
Should read:
-- When specifying an angle of diffraction 2theta ($2\theta$) for a --

Signed and Sealed this
Fourteenth Day of February, 2023

*Katherine Kelly Vidal*
*Director of the United States Patent and Trademark Office*

CERTIFICATE OF CORRECTION (continued)
U.S. Pat. No. 11,390,615 B2

Column 6, Lines 45-46:
"was run at of 40 kV/40 mA. A step size of 0.02° (20) and a step time of 76.8 sec over a scanning range of 3-50° in 20"
Should read:
-- was run at of 40 kV/40 mA. A step size of 0.02° ($2\theta$) and a step time of 76.8 sec over a scanning range of 3-50° in $2\theta$ --

Column 6, Line 53:
"evaluation software (EVA). The accuracy of the 20 values as"
Should read:
-- evaluation software (EVA). The accuracy of the $2\theta$ values as --

Column 7, Line 31:
"J=5.8 Hz, 1H), 4.21 (dd, =8.3 Hz, J$_2$=6.9 Hz, 1H), 3.98 (s,"
Should read:
-- J=5.8 Hz, 1H), 4.21 (dd, J$_1$=8.3 Hz, J$_2$=6.9 Hz, 1H), 3.98 (s, --

Column 7, Line 49:
"Hz, 1H), 4.23 (dd, =8.4 Hz, J$_2$=6.5 Hz, 1H), 4.01 (m, 4H),"
Should read:
-- Hz, 1H), 4.23 (dd, J$_1$=8.4 Hz, J$_2$=6.5 Hz, 1H), 4.01 (m, 4H), --